United States Patent
Fujita (10) Patent No.: US 8,070,760 B2
(45) Date of Patent: Dec. 6, 2011

(54) CLIPPING INSTRUMENT FOR AN ENDOSCOPIC SURGICAL DEVICE

(75) Inventor: Yasunobu Fujita, Tokyo (JP)

(73) Assignee: Hoya Corporation, Tokyo (JP)

( * ) Notice: Subject to any disclaimer, the term of this patent is extended or adjusted under 35 U.S.C. 154(b) by 524 days.

(21) Appl. No.: 12/250,744

(22) Filed: Oct. 14, 2008

(65) Prior Publication Data

US 2009/0105533 A1 Apr. 23, 2009

(30) Foreign Application Priority Data

Oct. 17, 2007 (JP) ................................ 2007-269731

(51) Int. Cl.
*A61B 17/10* (2006.01)
(52) U.S. Cl. ........ 606/142; 606/139; 606/151; 606/157; 606/158
(58) Field of Classification Search ................. 606/139, 606/142, 140, 151, 155, 157, 143, 158
See application file for complete search history.

(56) References Cited

U.S. PATENT DOCUMENTS

| | | | | |
|---|---|---|---|---|
| 4,458,682 | A | * | 7/1984 | Cerwin ......................... 606/158 |
| 5,366,459 | A | * | 11/1994 | Yoon ............................ 606/151 |
| 5,520,701 | A | * | 5/1996 | Lerch ........................... 606/142 |
| 5,634,932 | A | * | 6/1997 | Schmidt ........................ 606/157 |
| 5,725,542 | A | * | 3/1998 | Yoon ............................ 606/157 |
| 5,972,003 | A | * | 10/1999 | Rousseau et al. ............ 606/142 |
| 6,814,742 | B2 | * | 11/2004 | Kimura et al. ............... 606/151 |
| 7,011,667 | B2 | | 3/2006 | Kobayashi et al. |
| 2005/0080440 | A1 | * | 4/2005 | Durgin et al. ................ 606/157 |
| 2007/0049949 | A1 | | 3/2007 | Manetakis |
| 2007/0185504 | A1 | | 8/2007 | Manetakis et al. |
| 2007/0191868 | A1 | | 8/2007 | Theroux et al. |
| 2008/0114377 | A1 | | 5/2008 | Shibata et al. |

FOREIGN PATENT DOCUMENTS

| | | |
|---|---|---|
| JP | 2002-330972 | 11/2002 |
| JP | 2006-87537 | 4/2006 |
| JP | 2008-119068 | 5/2008 |

OTHER PUBLICATIONS

English language Abstract of JP 2002-330972, Nov. 19, 2002.
English language Abstract of JP 2006-87537, Apr. 6, 2006.
English language Abstract of JP 2008-119068, May 29, 2008.

* cited by examiner

*Primary Examiner* — Darwin Erezo
*Assistant Examiner* — Alexander Orkin
(74) *Attorney, Agent, or Firm* — Greenblum & Bernstein, P.L.C.

(57) ABSTRACT

A clipping instrument for an endoscope is provided. The clipping instrument includes a flexible sheath, an operation wire, at least one detachable clip assembly, including a pair of openable and closable clipping arms and a fastening ring, the clipping arms being configured to be projected forward to open and to be closed according to forwarding and retracting movements of the fastening ring through the operation wire, a withdrawal stopper and an advancement stopper, which are provided in the vicinity of the distal end portion of the flexible sheath. The withdrawal stopper restricts the fastening ring from being retracted rearward into the withdrawal stopper once the fastening ring is forwarded to penetrate through the withdrawal stopper. The advancement stopper restricts the fastening ring from being forwarded further to penetrate out of the advancement stopper once the fastening ring is forwarded to penetrate through the withdrawal stopper.

20 Claims, 13 Drawing Sheets

CLIPPING INSTRUMENT FOR AN ENDOSCOPIC SURGICAL DEVICE

BACKGROUND OF THE INVENTION

The present invention relates to a surgical device having a clipping instrument to be inserted through a forceps channel of an endoscope.

Generally, in a clipping instrument for endoscopic surgeries, a clip having a pair of openable/closable arms and a fastening ring loosely fit around proximal portions of the arms is arranged in a distal end portion of a flexible sheath. The clip is configured such that the arms open and close as an operation wire, arranged in parallel with an axial direction of the flexible sheath, is advanced toward the distal end to push the fastening ring and retracted toward a proximal end to pull the fastening ring. The clip can be detached from the operation wire with its arms closed according to the operations to the operation wire. Such a configuration of the clipping instrument is disclosed in Japanese Patent Provisional Publication No. 2006-87537, for example.

Figure 19:
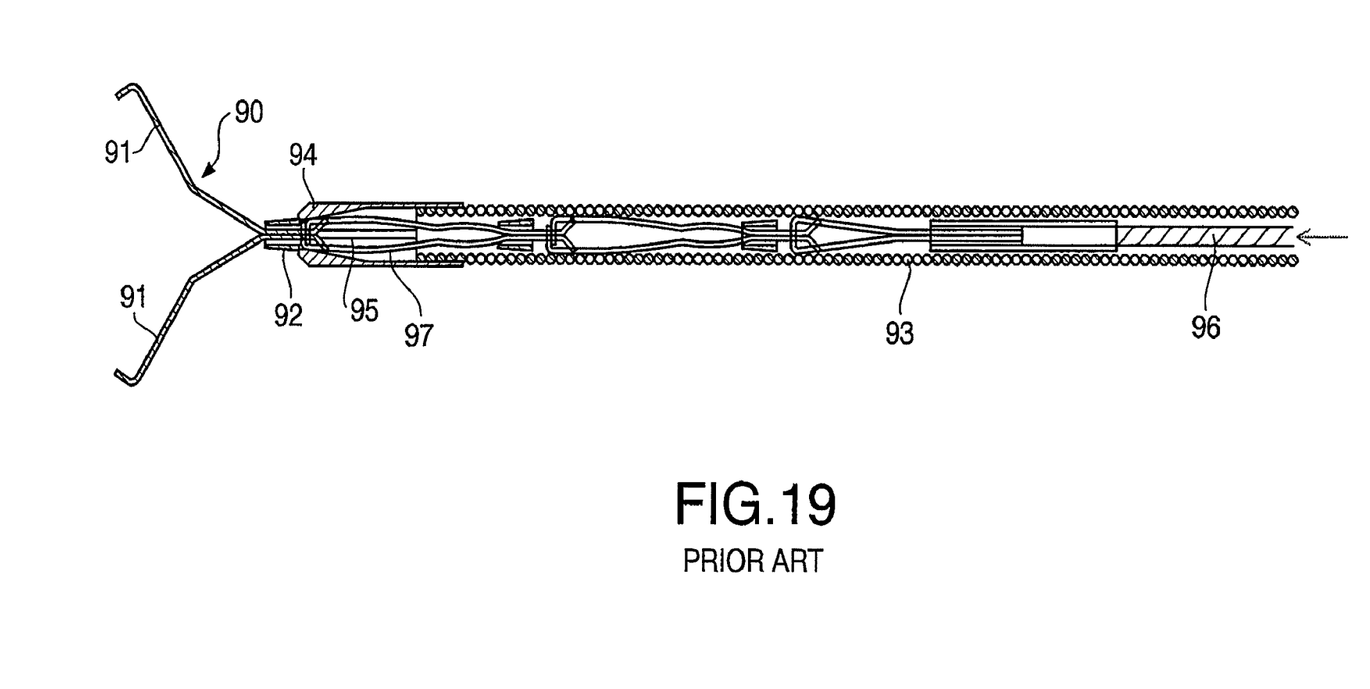
FIG. 19 is an overall cross-sectional side view of a conventional clipping instrument for an endoscope.

FIG. 19 shows a clipping instrument 90 disclosed in the above-referenced publication. A fastening ring 92 fit around a rear portion of openable arms 91 is pushed out of a sleeve 94, which is provided at a distal end of a flexible sheath 93.

The sleeve 94 is formed to have a plurality of slits, which are parallel to an axial direction, so that the fastening ring 92 can resiliently outstretch the sleeve 94 and penetrate therethrough, and the arms 91 can be maintained open.

When the fastening ring 92 passes through the sleeve 94 completely, the resiliently deformed sleeve 94 restores to the original shape, and the fastening ring 92 is restricted from being pulled back into the sleeve 94. Therefore, when an operation wire 96 is pulled toward the proximal end, the arms 91 are pulled in the fastening ring 92 and forcibly closed to clutch onto the body tissue.

When the operation wire 96 is again pushed forward, hooks 97, which are arms of a succeeding clip, are pushed out of the sleeve 94, and the clip 90 is detached from the hooks 97 to be left clutched during the surgery. Thus, an endoscopic clipping operation is conducted.

In the above clipping operation, however, when the fastening ring 92 following the arms 91 is pushed forward to be out of the sleeve 94, considerable force to widen the slits 95 to deform the sleeve 94 is required.

Therefore, when the fastening ring 91 is pushed forward with unintentional excessive force, the clip 90 may be pushed out of the sleeve 94 entirely to be unreturnable in the sleeve 94. In such a case, the arms 91 can no longer be closed.

SUMMARY OF THE INVENTION

In view of the foregoing drawback, the present invention is advantageous in that an endoscopic surgical device with a clipping instrument, of which fastening ring can steadily stop at a predetermined position and be prevented from being advanced further from the predetermined position, and of which arms can be easily and securely opened and closed, is provided.

According to an aspect of the present invention, a clipping instrument for an endoscope is provided. The clipping instrument includes a flexible sheath to be inserted into an instrument channel of the endoscope, an operation wire, which is configured to be forwarded and retracted in an axial direction of the flexible sheath, at least one detachable clip assembly, including a pair of openable and closable clipping arms and a fastening ring to encircle proximal portions of the clipping arms, arranged in the vicinity of a distal end portion of the flexible sheath with the clipping arms closed, the clipping arms being configured to be projected forward to open outside the flexible sheath and to be closed to clip onto a treatment object outside the flexible sheath according to forwarding and retracting movements of the fastening ring through the operation wire, a withdrawal stopper, which is provided in the vicinity of the distal end portion of the flexible sheath, and an advancement stopper, which is provided in the vicinity of the distal end portion of the flexible sheath. The withdrawal stopper restricts the fastening ring from being retracted rearward into the withdrawal stopper once the fastening ring is forwarded to penetrate through the withdrawal stopper. The advancement stopper restricts the fastening ring from being forwarded further to penetrate out of the advancement stopper once the fastening ring is forwarded to penetrate through the withdrawal stopper.

Optionally, the withdrawal stopper may be axially movable with respect to the advancement stopper. The advancement stopper may be at least partially fixed with respect to the flexible sheath. The advancement stopper may permit the fastening ring to be forwarded further to penetrate out of the advancement stopper when the withdrawal stopper is moved rearward with respect to the advancement stopper according to the retracting movement of the fastening ring, which once has been forwarded to penetrate through the withdrawal stopper.

Optionally, The withdrawal stopper may include a pair of blade springs, and the advancement stopper may include a different pair of blade springs, which are radially expanded with respect to an axis of the flexible sheath.

Optionally, the blade springs of the withdrawal stopper may be formed to extend from a trunk portion toward a front of the clipping instrument, and front portions of the blade springs resiliently may press sides of the clip assembly.

Optionally, the pair of clipping arms may be opened as the fastening ring, which is restricted from being forwarded by the advancement stopper, is pushed forward by the operation wire due to transition of contact points of the fastening ring with the pair of clipping arms.

Optionally, the pair of once opened clipping arms may be closed as the fastening ring, which is restricted from being forwarded by the advancement stopper, is retracted rearward by the operation wire due to transition of contact points of the fastening ring with the pair of clipping arms.

Optionally, the advancement stopper may be fixed with respect to the flexible sheath at a rear end portion thereof. Distal ends of the blade springs of the advancement stopper may be angled inward so that the fastening ring is prevented from being further forwarded when the withdrawal stopper is moved toward the front of the clipping instrument with respect to the advancement stopper to be in a tightening position.

Optionally, the withdrawal stopper may apply tightening force to the advancement stopper to restrict the advancement of the fastening ring when the withdrawal stopper is moved to the tightening position to at least partially cover and resiliently tighten the blade springs of the advancement stopper. The advancement stopper may be released from the tightening force when the withdrawal stopper is retracted rearward with respect to the advancement stopper according to the retracting movement of the fastening ring and restored to be expanded so that the fastening ring is permitted to be forwarded further to penetrate out of the advancement stopper.

Optionally, the advancement stopper may be restricted from being rotated about an axis of the flexible sheath.

Optionally, the withdrawal stopper may be restricted from being rotated about an axis of the flexible sheath.

Optionally, the withdrawal stopper may be restricted from being rotated with respect to the advancement stopper.

Optionally, the blade springs of the advancement stopper may be provided in symmetric positions at approximately 180 degrees from each other. The blade springs of the withdrawal stopper may be provided in symmetric positions at approximately 180 degrees from each other. The withdrawal stopper and the advancement stopper may be assembled together such that the blade springs of the withdrawal stopper are in positions to define approximately 90 degrees with the blade springs of the advancement stopper respectively.

Optionally, the clipping instrument may further include a sleeve, which is provided in the vicinity of the distal end portion of the flexible sheath and fixed to the flexible sheath, to support the advancement stopper and the withdrawal stopper.

Optionally, the advancement stopper may be fixed to the sleeve at least partially at the trunk portion, and the withdrawal stopper may be axially movably fit around the advancement stopper.

Optionally, the sleeve may be formed to have a pair of slits, in which at least parts of the blade springs of the withdrawal stopper are movable, extending in the axial direction of the flexible sheath in symmetric positions at approximately 180 degrees from each other.

Optionally, the sleeve may be formed to have a pair of cutout portions, in which distal end portions of the advancement stopper can be fit, in symmetric positions at approximately 180 degrees from each other and at approximately 90 degrees from the respective slits.

Optionally, the advancement stopper may be assembled with the sleeve to have the distal end portions thereof aligned in a substantially same plane with a distal end portion of the sleeve.

DETAILED DESCRIPTION OF THE EMBODIMENT

Figure 1:
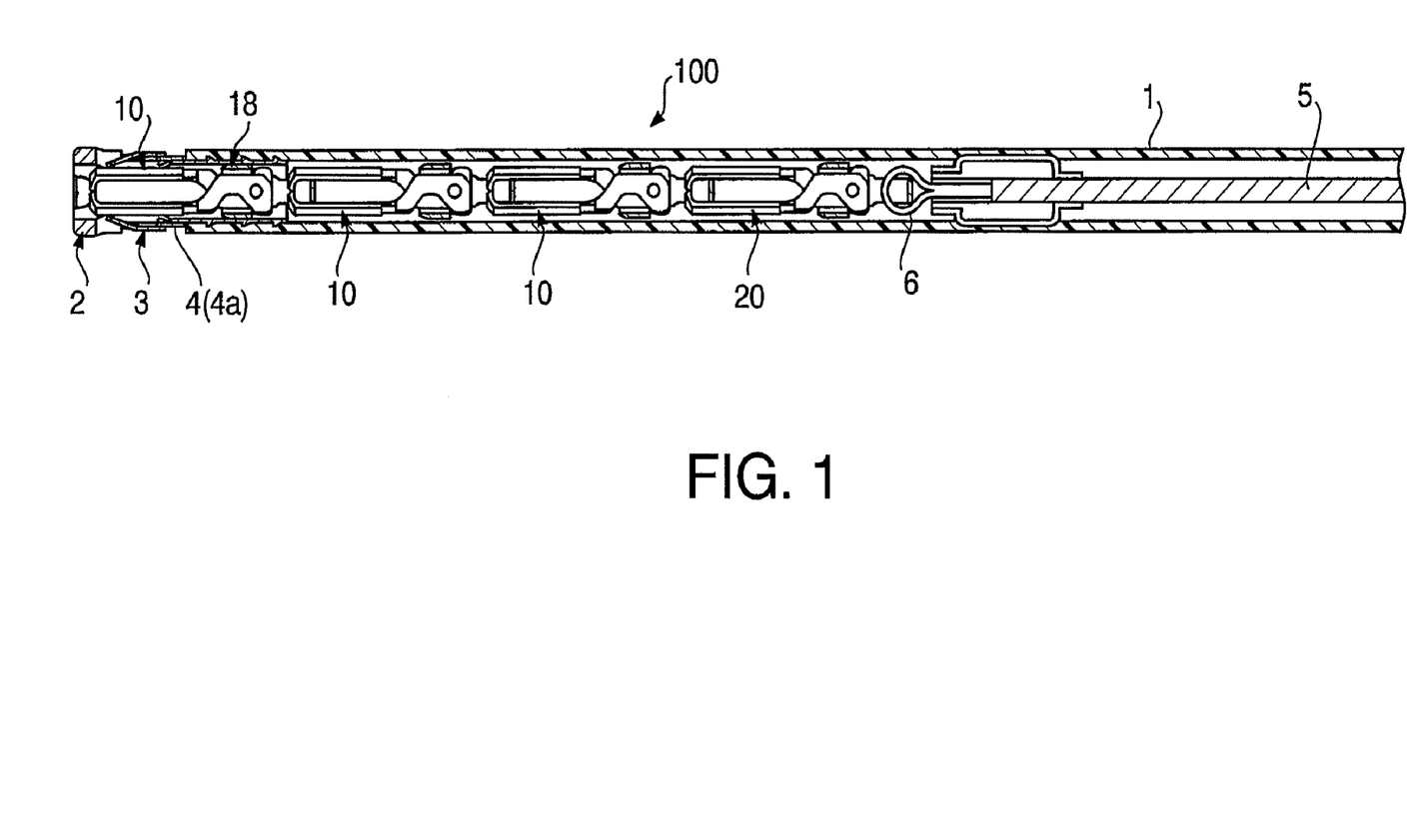
FIG. 1 is an overall cross-sectional side view of a clipping instrument with clip assemblies aligned in a flexible sheath according to an embodiment of the present invention.
Figure 2:
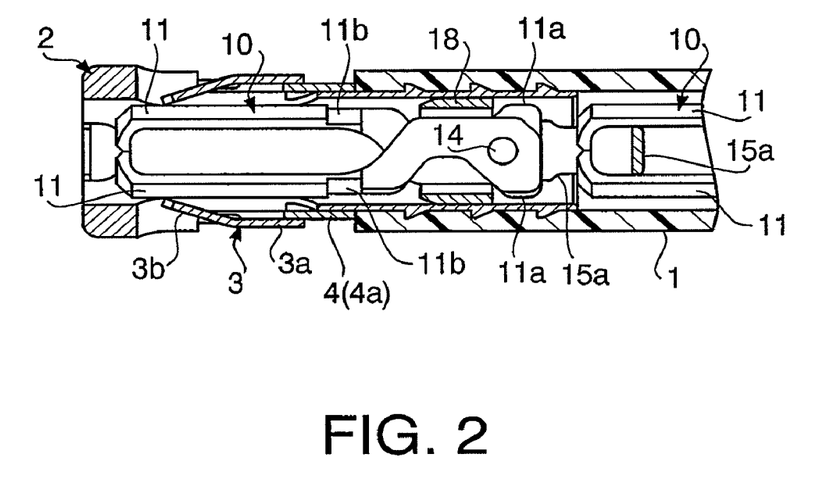
FIG. 2 is a partial and cross-sectional side view of a front end clip assembly being closed in the flexible sheath of the clipping instrument according to the embodiment of the present invention.

Hereinafter, referring to the accompanying drawings, an illustrative embodiment of the invention will be described. FIG. 1 is an overall cross-sectional side view of a clipping instrument 100 with clip assemblies 10 in a flexible sheath 1 according to an embodiment of the present invention. FIG. 2 is a partial and cross-sectional side view of a front end clip assembly 10 being closed in the flexible sheath 1 according to the embodiment of the present invention.

The flexible sheath 1 is made of, for example, poly-tetra-fluoro-ethylene and is inserted into a forceps channel (not shown) of an endoscope (not shown).

The flexible sheath 1 is provided with a sleeve 2, which is made of a metal (e.g., stainless steel) or hard resin, at a distal end.

Inside the flexible sheath 1, an operating wire 5 to be advanced and retracted in parallel with the axial direction of the flexible sheath 1 is provided. The operating wire 5 is connected to an operating unit (not shown) at a proximal end thereof and can be advanced and retracted in accordance with an operation given to the operating unit. The operating wire 5 is fixedly connected to a connecting loop 6.

Figure 3:
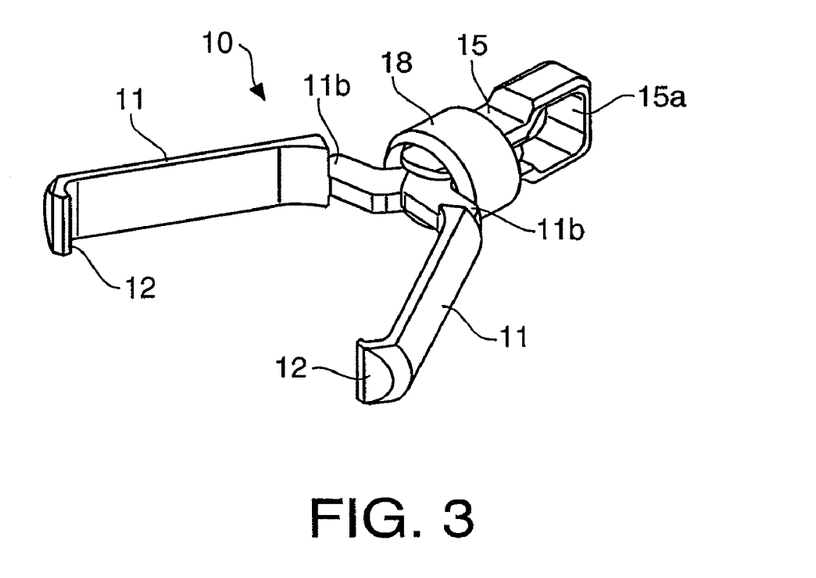
FIG. 3 is a perspective view of one of the clip assemblies in the clipping instrument according to the embodiment of the present invention.
Figure 4:
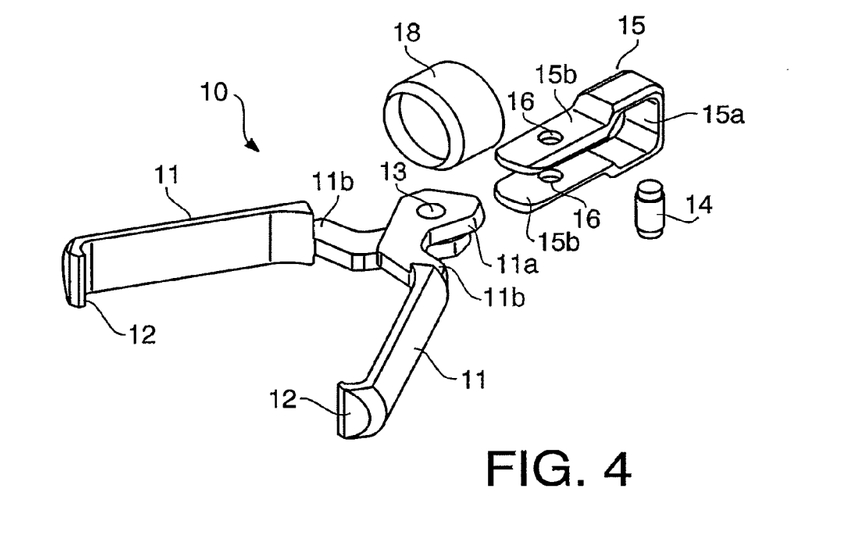
FIG. 4 is an exploded view of one of the clip assemblies in the clipping instrument according to the embodiment of the present invention.

Further inside the flexible sheath 1, in vicinity to a distal end portion thereof, a plurality of clip assemblies 10 are aligned in line. FIG. 3 is a perspective view of one of the clip assemblies 10 in the clipping instrument 100 according to the embodiment of the present invention. FIG. 4 is an exploded view of one of the clip assemblies 10 in the clipping instrument 100 according to the embodiment of the present invention. The clip assembly 10 is provided with a pair of arms 11, each of which is individually formed and provided with a claw portion 12. The claw portion 12 is curved inward, when the arms 11 are assembled, so that the two claws 12 are opposed to each other to clutch a treatment object.

Each of the arms 11 is formed to have a through hole 13 in vicinity to a proximal end thereof. A shaft 14 supporting the arms 11 is penetrated through the through holes 13 of the arms 11 so that the arms 11, rotated about the shaft 14, can be arbitrarily opened and closed.

The clip assembly 10 is further provided with a tail portion 15, which includes an open-ringed connecting loop 15a at a proximal end thereof, a pair of plate portions 15b, which are parallel to each other and loosely nip the proximal end portion of the arms 11 therebetween, and through holes 16 through which the shaft 14 is penetrated. The tail portion 15 is connected to the operating wire 5 through another clip assembly 10 being aligned at a proximal side and a connecting clip 20, which will be described later.

Furthermore, the clip assembly 10 includes a fastening ring 18, by which the arms 11 are forcibly closed. When the arms 11 are allowed to be open, the fastening ring 18 is loosely fit around the proximal portion of the arms 11, as shown in FIG. 2.

When the fastening ring 18 is retracted rearward to an opening position shown in FIG. 3, in which the fastening ring 18 becomes in contact with cam portions 11a of the arms 11, contact points of the fastening ring 18 with the arms 11 shift gradually, and the arms 11 are opened due to the transition of the contact points. In reverse, when the fastening ring 18 is forwarded, the arms 11 are forcibly closed. When the fastening ring 18 is forwarded to press end portions 11b of the arms 11, the arms 11 are fully and irreversibly closed.

Figure 5:
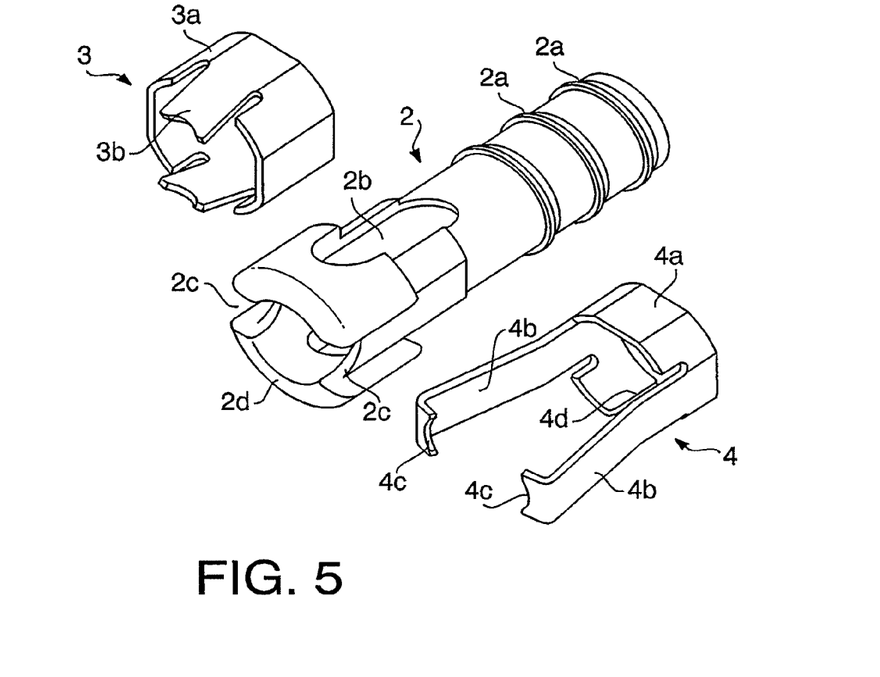
FIG. 5 is an exploded view of a sleeve, a withdrawal stopper, and an advancement stopper to be arranged in a distal end portion of the flexible sheath of the clipping instrument according to the embodiment of the present invention.

FIG. 5 is an exploded view of the sleeve 2, a withdrawal stopper 3, and an advancement stopper 4 to be arranged in a distal end portion of the flexible sheath 1 of the clipping instrument 100 according to the embodiment of the present invention. A proximal half portion of the sleeve 2 is formed to be substantially cylindrical and fixedly inserted into the flexible sheath 1. The proximal half portion includes stops 2a to be wedged into an inner surface of the flexible sheath 1 so that the sleeve 2 can be prevented from falling off from the flexible sheath 1.

The withdrawal stopper 3 prevents the clip assembly located in the sleeve 2 from being swayed. Further, once the fastening ring is forwarded to be entirely out of the sleeve 2, the proximal end of the fastening ring 18 comes into contact with the withdrawal stopper 3 so that the fastening ring 18 can be prevented from being withdrawn again in the sleeve 2.

The withdrawal stopper 3 is formed to have a ring-like trunk portion 3a, which is axially movably fit partially around the advancement stopper 4, and a pair of integrally formed blade springs 3b, which are in symmetric positions at approximately 180 degrees from each other. The blade springs 3b extend from the trunk portion 3a toward a front of the clipping instrument 100 and are angled inward. Distal end portions of the blade springs 3b resiliently press sides of the clip assembly 10 constantly so that the clip assembly is held steadily without swaying.

The advancement stopper 4 prevents the fastening ring 18, which has penetrated through the withdrawal stopper 3, from being further advanced. The advancement stopper 4 is formed to have a C-shaped portion 4a, which is fixedly fit partially around the sleeve 2, and a pair of integrally formed blade springs 4b, which extend from the C-shaped portion 4a toward the front of the clipping instrument 100 and are in symmetric positions at approximately 180 degrees from each other. Distal ends of the blade springs 4b are angled inward to form claws 4c so that the fastening ring 18 can be stopped thereat and prevented from being further advanced.

The advancement stopper 4 is provided with an axially-formed cut 4d, which enables the C-shaped portion 4a to be resiliently deformed when the advancement stopper 4 is assembled with the sleeve 2.

It is to be noted, however, as shown in FIG. 5, the pair of blade springs 4b are formed to expand radially from the C-shaped portion 4a toward the distal ends with respect to the axis of the C-shaped portion 4a (i.e., the axis of the flexible sheath 1) in the original state, and the claws 4c are not in contact with the fastening ring 18; therefore, the fastening ring 18 cannot be stopped thereat by the blade springs 4b.

The sleeve 2 is formed to have slits 2b with substantial widths, which are in symmetric positions at approximately 180 degrees from each other, and the blade springs 3b of the withdrawal stopper 3 can be movably inserted in the slits 2b. Further, a pair of cutout portions 2c are formed in symmetric positions at approximately 180 degrees from each other, and at approximately 90 degrees from the slits 2b. Each of the claws 4c of the advancement stopper 4 is movably fit in each cutout portion 2c. The sleeve 2 further includes distal end portions 2d.

Figure 6:
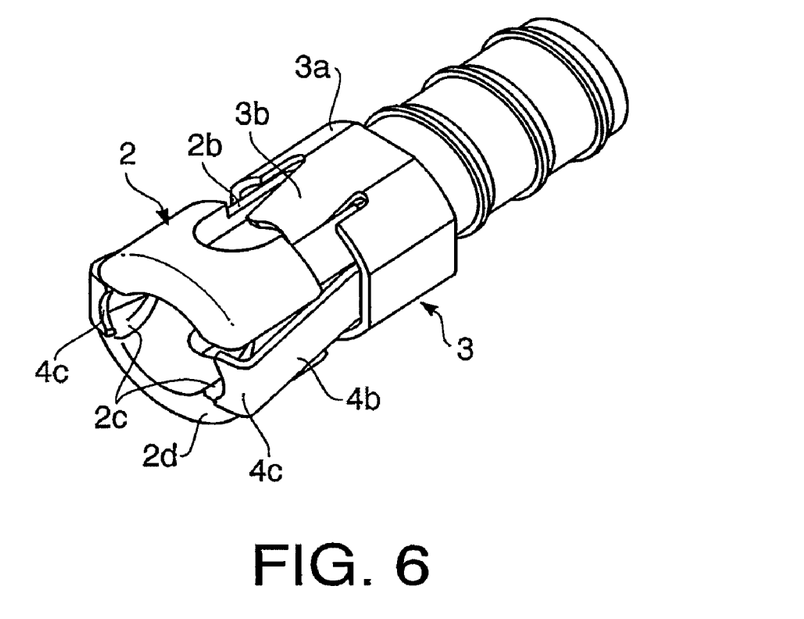
FIG. 6 is a perspective view of the sleeve with the withdrawal stopper and the advancement stopper assembled together according to the embodiment of the present invention.

FIG. 6 is a perspective view of the sleeve 2 with the withdrawal stopper 3 and the advancement stopper 4 assembled together according to the embodiment of the present invention. The C-shaped portion 4a of the advancement stopper 4 is fixed to an outer peripheral surface of the sleeve 2 at least partially by, for example, laser welding, and the trunk portion 3a of the withdrawal stopper 3 is fit substantially around the C-shaped portion 4a of the advancement stopper 4.

Figure 8:
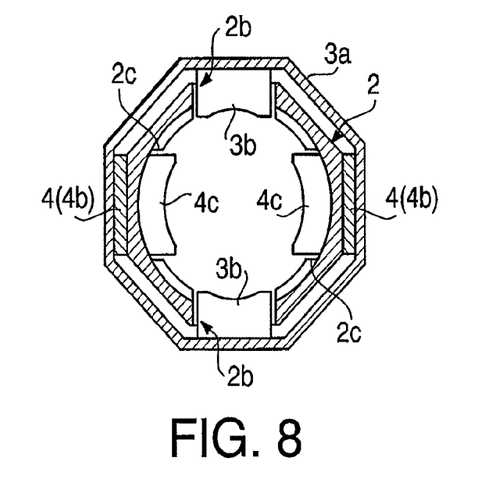
FIG. 8 is a cross-sectional view of the sleeve, the withdrawal stopper, and the advancement stopper assembled together, taken in a line VIII-VIII indicated in FIG. 7.

In the present embodiment, peripheral surfaces of the trunk portion 3a of the withdrawal stopper 3 and the C-shaped portion 4a of the advancement stopper 3a are formed to be noncircular, e.g., octagonal, so that the withdrawal stopper 3 cannot be rotated about an axis with respect to the advancement stopper 4, while the withdrawal stopper 3 can be moved in the axial direction with respect to the advancement stopper 4 (see FIG. 8). The withdrawal stopper 3 is assembled with the advancement stopper 4 such that the blade springs 3b of the withdrawal stopper 3 are in positions to define approximately 90 degrees with the blade springs 4b of the advancement stopper 4 respectively.

When the withdrawal stopper 3 is set in place as shown in FIG. 6, the trunk portion 3a of the withdrawal stopper 3 does not cover the blade springs 4b of the advancement stopper 4. Therefore, the blade springs 4b remain expanded radially, and the fastening ring 18 is permitted to pass through the clearance between the claws 4c of the blade springs 4b. The blade springs 3b being angled inward are inserted in the slits 2b.

Figure 7:
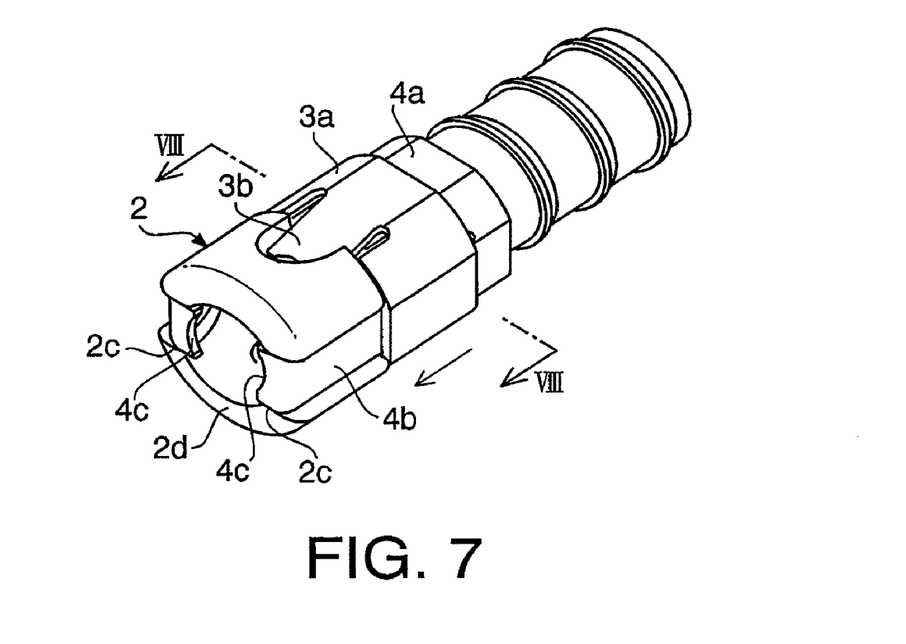
FIG. 7 is a perspective view of the sleeve with the withdrawal stopper forwarded with respect to the advancement stopper in the clipping instrument according to the embodiment of the present invention.

When the withdrawal stopper 3 is forwarded in the axial direction along the peripheral surface of the advancement stopper 4 to a tightening position (see FIG. 7), the trunk portion 3a of the withdrawal stopper 3 partially covers to apply tightening force and tightens the blade springs 4b of the advancement stopper 4 inward. FIG. 7 is a perspective view of the sleeve 2 with the withdrawal stopper 3 forwarded with respect to the advancement stopper 4 in the tightening position in the clipping instrument 100 according to the embodiment of the present invention. FIG. 8 is a cross-sectional view of the sleeve 2, the withdrawal stopper 3, and the advancement stopper 4 assembled together, taken in a line VIII-VIII indicated in FIG. 7.

With the blade springs 4b partially covered with the trunk portion 3a of the withdrawal stopper 3, the blade springs 4b are resiliently deformed inwardly so that the claws 4c are housed in the cutout portions 2c of the sleeve 2. Thus, the fastening ring 18 is restricted from being advanced further from the claws 4c of the advancement stopper 4, and the claws 4c at the distal ends of the blade springs 4b become aligned substantially in a same plane with the distal end portions 2d of the sleeve 2.

In order to prevent the withdrawal stopper 3 in the forwarded position from being rotated about the axis with respect to the sleeve 2, a periphery of a portion of the sleeve 2 around which the withdrawal stopper 3 is fit is also formed to be substantially octagonal (see FIG. 5).

When the trunk portion 3a of the withdrawal stopper 3 is retracted rearward with respect to the advancement stopper 4, the blade springs 4b are released from the fastening force of the withdrawal stopper 3, and the fastening ring 18 is again permitted to be forwarded (see FIG. 6).

Referring back to FIGS. 1 and 2, in the flexible sheath 1 at the distal end portion, the clip assemblies 10 aligned in line are mutually connected. More specifically, the tail portion 15 of the clip assembly 10 in a position closer to the distal end of the flexible sheath 1 (front side) and the arms 11 of the clip assembly 10 in a position closer to the proximal end of the flexible sheath 1 (rear side) define a connected portion. The claws 12 of the arms 11 of the clip assembly 10 in the rear side are closed to clutch the connecting loop 15a of the clip assembly 10 positioned in the front side.

The clipping instrument 100 includes an undetachable clip assembly 20, which is undetachably connected to the connecting loop 6. Unlike the clip assemblies 10, the undetachable clip assembly 20 does not include the fastening ring 18; however, the remaining configuration of the detachable clip assembly 20 is identical to the clip assembly 10. The undetachable clip assembly 20 is connected to the tail portion 15 of the clip assembly 10 being located at the rear end of the aligned clip assemblies 10, i.e., the arms 11 of the undetachable clip assembly 20 are closed to clutch the tail portion 15 of the clip assembly 10 at the rear end.

The arms 11 of the plurality of mutually connected clip assemblies 10 and the undetachable clip assembly 20 are closed inside the flexible sheath 1 so that the clipping instrument 100 is inserted into the forceps channel of the endoscope.

Operations of the clipping instrument 100 configured as above in use in the forceps channel will be described with reference to FIGS. 1-2 and 9-18.

Figure 9:
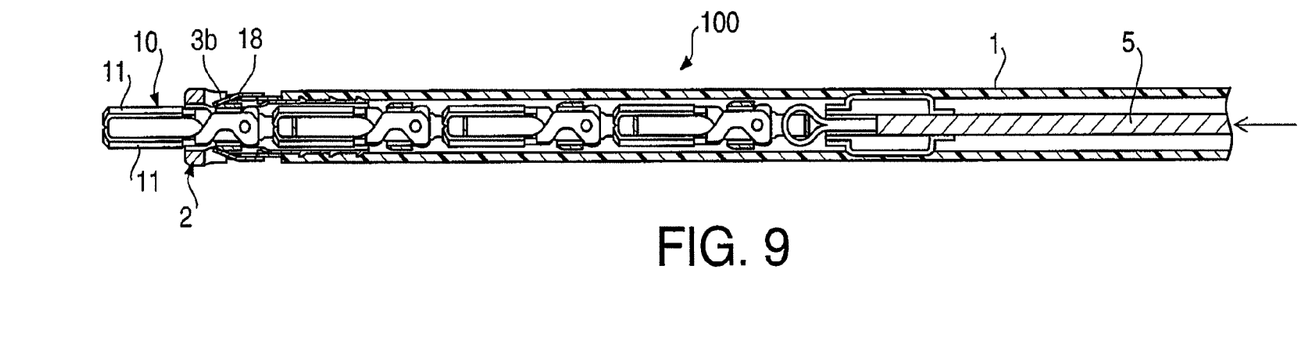
FIG. 9 is a cross-sectional side view of the clipping instrument with one of the clip assemblies projecting out of the flexible sheath of the clipping instrument according to the embodiment of the present invention.
Figure 10:
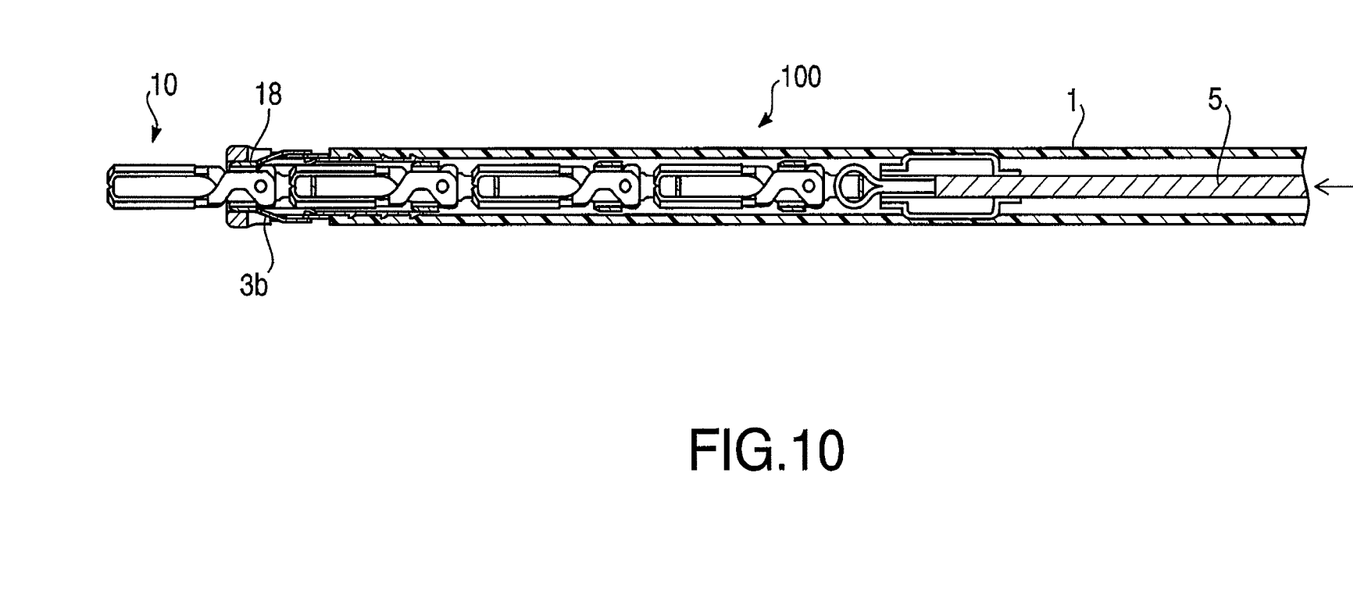
FIG. 10 is a cross-sectional side view of the clipping instrument with one of the clip assemblies projecting out of the flexible sheath of the clipping instrument according to the embodiment of the present invention.

FIGS. 9 and 10 are cross-sectional side views of the clipping instrument 100 in operation according to the embodiment of the present invention. When the flexible sheath 1 is inserted into the forceps channel of the endoscope, as shown in FIGS. 1 and 2, the clip assembly 10 at the front is entirely included in the flexible sheath 1. When the flexible sheath 1 in the forceps channel is brought in the vicinity of the treatment area, the operation wire 4 is advanced from the proximal end (see FIG. 9) so that the front clip assembly 10 is projected out of the flexible sheath 1 and the arms 11 are opened gradually.

In this state, the withdrawal stopper 3 is in the forwarded position with respect to the advancement stopper 4 (see FIG. 7); therefore, the fastening ring 18 is restricted from being forwarded.

As the arms 11 in the clip assembly 10 are pushed forward, slidably passing through the clearance between the claw portions 3b, the arms 11 are projected outward from the sleeve 2. Further, as shown in FIG. 10, the fastening ring 18 in the clip assembly is projected out of the sleeve 2 through the claw portions 3b.

Figure 11:
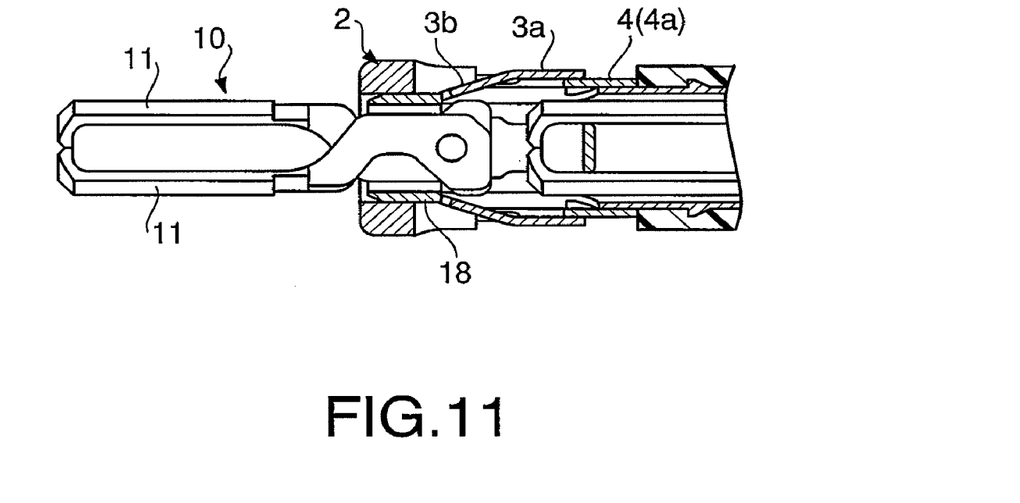
FIG. 11 shows an enlarged view of the clip assembly projecting out of the sleeve through the claw portions in the clipping instrument according to the embodiment of the present invention.

FIG. 11 shows an enlarged view of the clip assembly 10 projecting out of the sleeve 2 through the claw portions 3b in the clipping instrument 100 according to the embodiment of the present invention. As the clip assembly 10 is pushed forward, the claw portions 3b are resiliently deformed to trace the outlines of the clip assembly 10 until finally become in contact with the proximal end surface of the fastening ring 18. In this position, the fastening ring 18 is pressed to the claw portions 3b when the fastening ring 18 is pulled rearward; therefore, the fastening ring 18 is not permitted to be pulled back through the clearance between the claw portions 3b.

Figure 12:
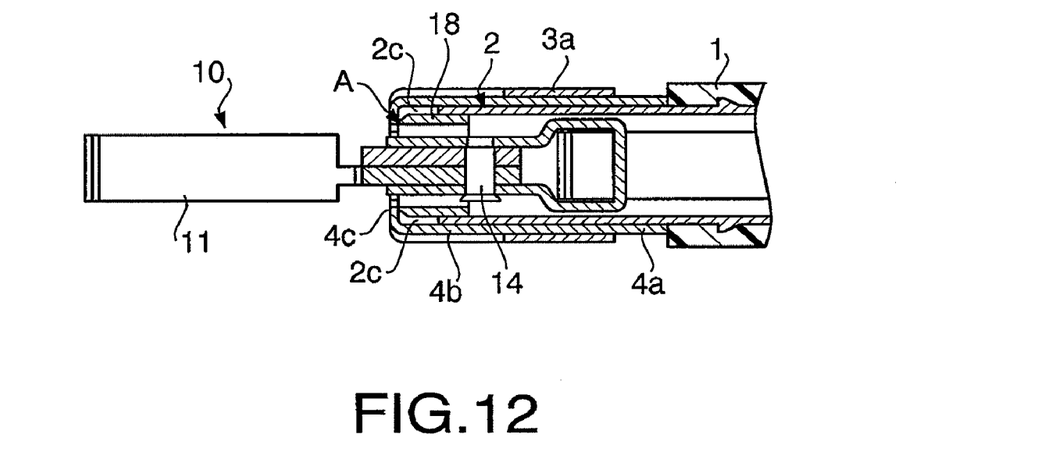
FIG. 12 shows a cross-sectional view of the clip assembly projecting out of the flexible sheath of the clipping instrument according to the embodiment of the present invention.

FIG. 12 shows a cross-sectional view of the clip assembly 10 projecting out of the sleeve 2 through the claw portions 3b in the clipping instrument 100 according to the embodiment of the present invention. As shown in FIG. 12, the blade springs 4b are closed by the trunk portion 3a of the withdrawal stopper 3, and the distal end surface of the fastening ring is in contact with the claws 4c of the advancement stopper 4 at a position A.

Thus, the blade springs 4b of the advancement stopper 4 restricts the fastening ring 18 from being advanced, and the fastening ring 18 can be securely stopped at the position A even when forwarding force is applied to the fastening ring 18 through the operation wire 5. Therefore, succeeding operations to open and close the following clip assembly 10 can be securely conducted.

Figure 13:
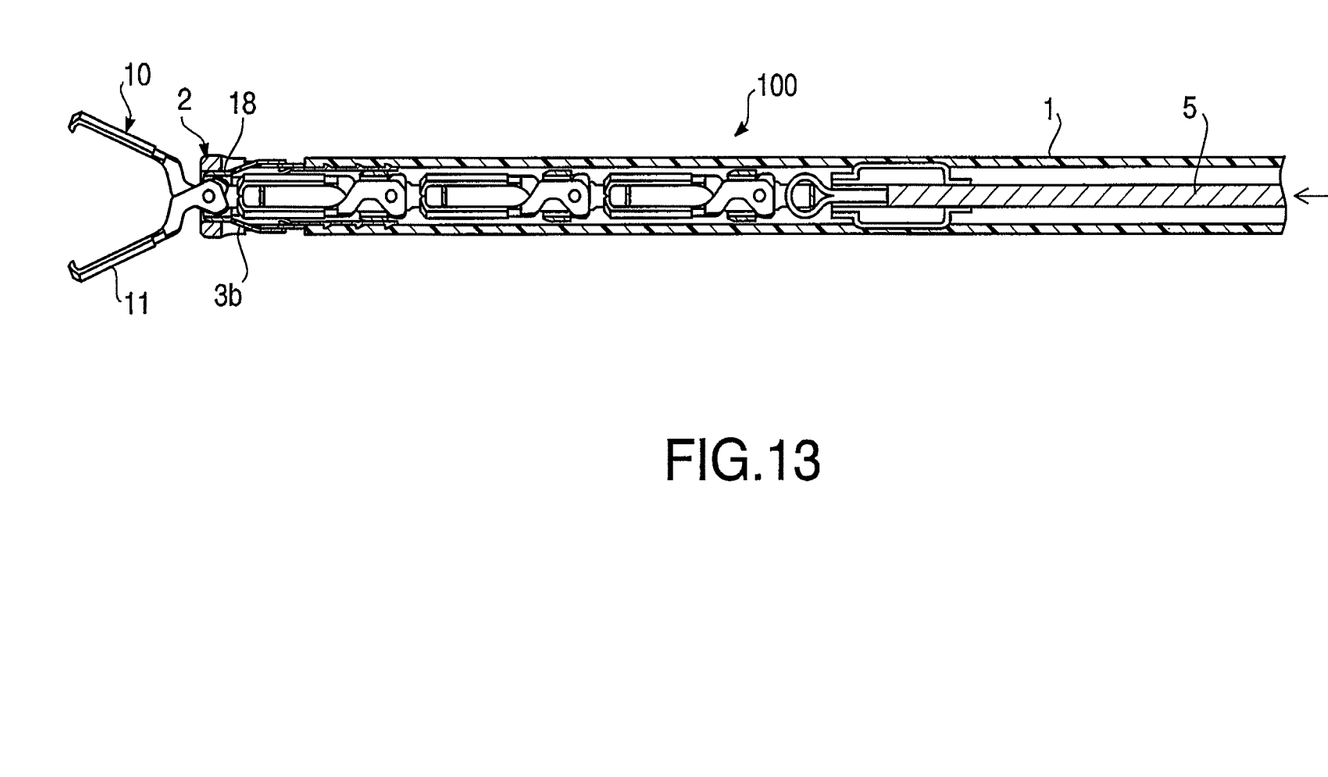
FIG. 13 shows a cross-sectional side view of the arms of the clip assembly being open outside the flexible sheath of the clipping instrument according to the embodiment of the present invention.

With the blade springs 4b and the fastening ring 18 in the above positions, the distal ends of the claw portions 3b resiliently presses the clip assembly 10 at the distal end surface of the fastening ring 18 (see FIG. 11). When the operation wire 5 is further advanced, the fastening ring 18 becomes in contact with cam portions 11a of the arms 11, and the arms 11 are opened. FIG. 13 shows a cross-sectional view of the arms 11 of the clip assembly 10 being open outside the flexible sheath 1 of the clipping instrument 100 according to the embodiment of the present invention.

With the clip assembly 10 projecting out of the flexible sheath 1, when the operation wire 5 is axially rotated according to an operator's manipulation through the operating unit, the clip assembly 10 is rotated as well so that the orientation of the arms 11 can be adjusted.

Figure 14:
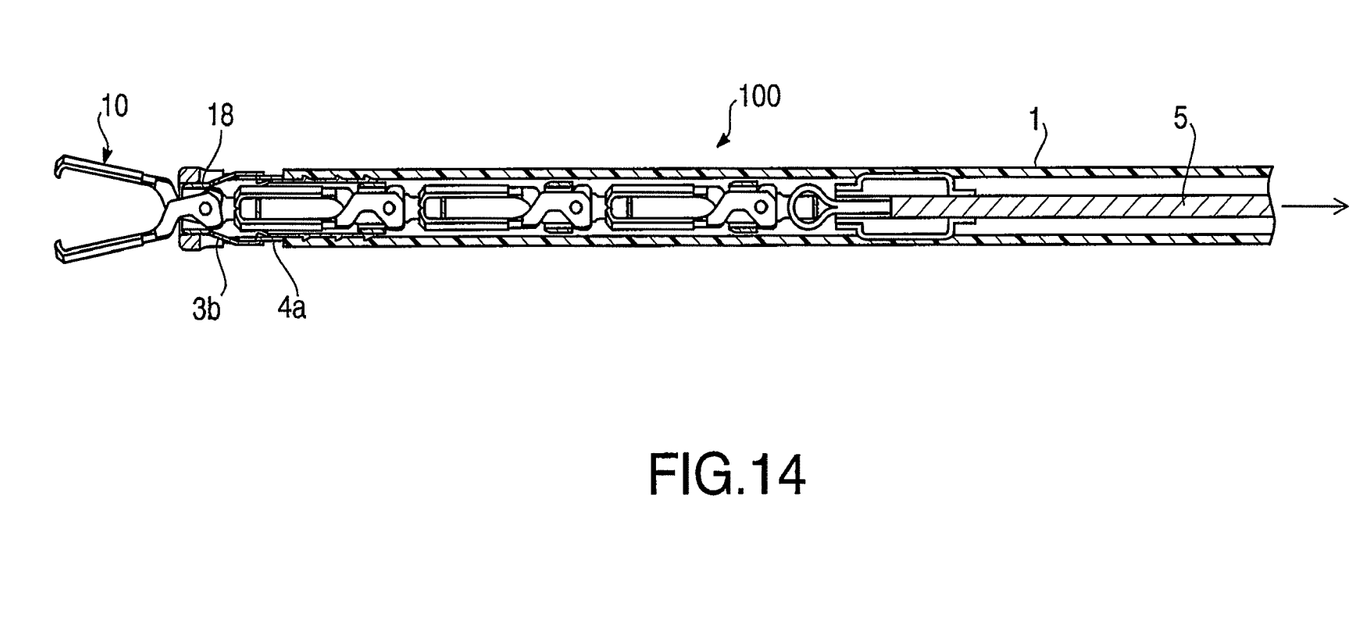
FIG. 14 shows a cross-sectional side view of the clipping instrument with the arms of the clip assembly being closed according to the embodiment of the present invention.

When the clip assembly 10 is brought to be substantially close to a treatment target (e.g., a diseased area of mucous membranes) to be clipped, the operation wire 5 can be withdrawn to the proximal end so that the arms 11 are forcibly closed by the fastening ring 18. FIG. 14 shows a cross-sectional side view of the clipping instrument 100 with the arms 11 of the clip assembly being closed according to the embodiment of the present invention.

If the operator is urged to correct an orientation of the clipping assembly 10 with respect to the treatment area, the operation wire 5 can be advanced forward to bring the clip assembly 10 in the position shown in FIG. 13 to repeat opening and closing operations of the arms 11.

Figure 15:
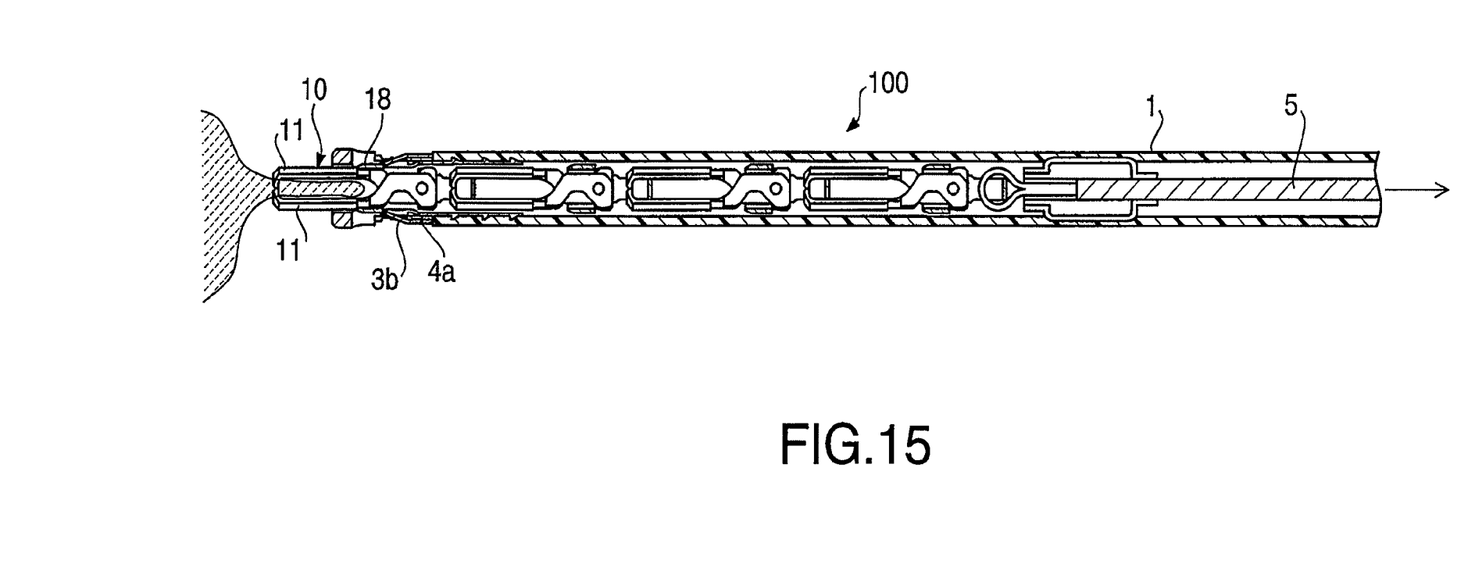
FIG. 15 shows a cross-sectional side view of the clipping instrument with the arms of the clip assembly being closed to clutch a treatment area according to the embodiment of the present invention.
Figure 16:
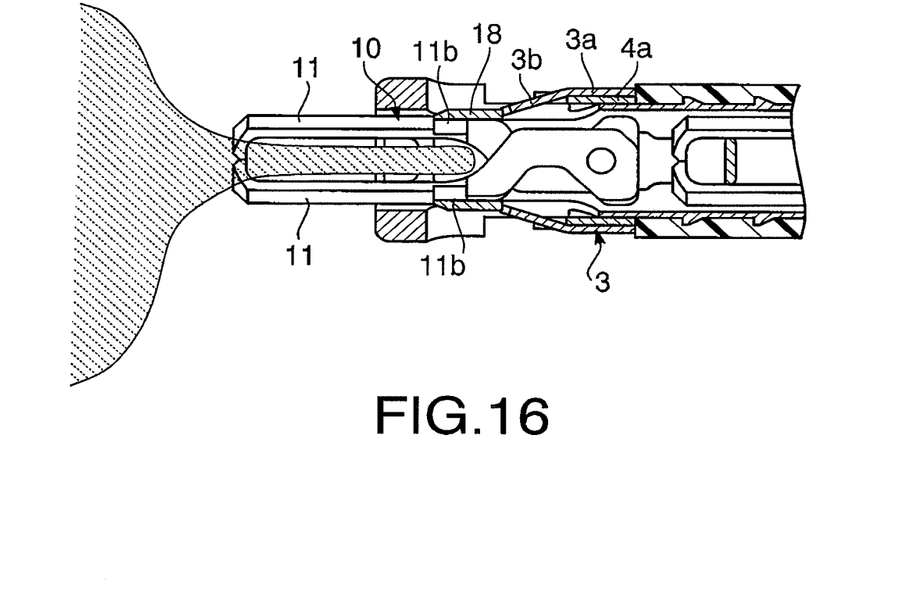
FIG. 16 is an enlarged cross-sectional side view of the clipping instrument with the arms being closed to clutch the treatment area according to the embodiment of the present invention.

When the arms 11 are pressed to clutch onto the treatment area, the operation wire 5 is withdrawn to the proximal end so that the arms 11 can be closed. FIG. 15 shows a cross-sectional side view of the clipping instrument 100 with the arms 11 of the clip assembly 10 being closed to clutch the treatment area according to the embodiment of the present invention, and FIG. 16 is an enlarged view of the clipping instrument 100 with the arms 11 being closed to clutch the treatment area according to the embodiment of the present invention.

As shown in FIG. 6, when the fastening ring 18 is withdrawn to press end portions 11b of the arms 11, the arms 11 are fully and irreversibly closed. Simultaneously, the withdrawal stopper 3 is retracted to a rearmost position in a movable range with respect to the advancement stopper 4 so that the fastening ring 18 as well as the withdrawal stopper 3 is restricted from being moved further toward the proximal end. The rearmost position in the movable range of the withdrawal stopper 3, according to the present embodiment, is defined by the distal end of the flexible sheath 1 with which the proximal end of the trunk portion 3a becomes in contact. However, the rearmost position may be defined by, for example, a protrusion formed on the surface of the sleeve 2.

Figure 17:
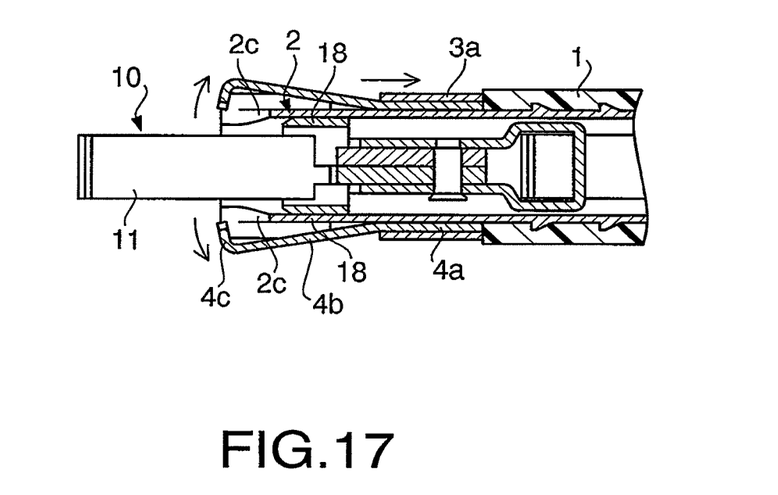
FIG. 17 shows a cross-sectional view of the clip assembly with the blade springs of the advancement stopper being released from the withdrawal stopper of the clipping instrument according to the embodiment of the present invention.

FIG. 17 shows a cross-sectional view of the clip assembly 10 with the blade springs 4b of the advancement stopper 4 being released from the withdrawal stopper 3 of the clipping instrument 100 according to the embodiment of the present invention. As shown in FIG. 17, when the withdrawal stopper 3 is retracted to the rearmost position, the blade springs 4b of the advancement stopper 4 are released from the fastening force of the trunk portion 3a and restored to the expanded form. Therefore, the fastening ring 18 is permitted to be advanced (see FIG. 6).

Figure 18:
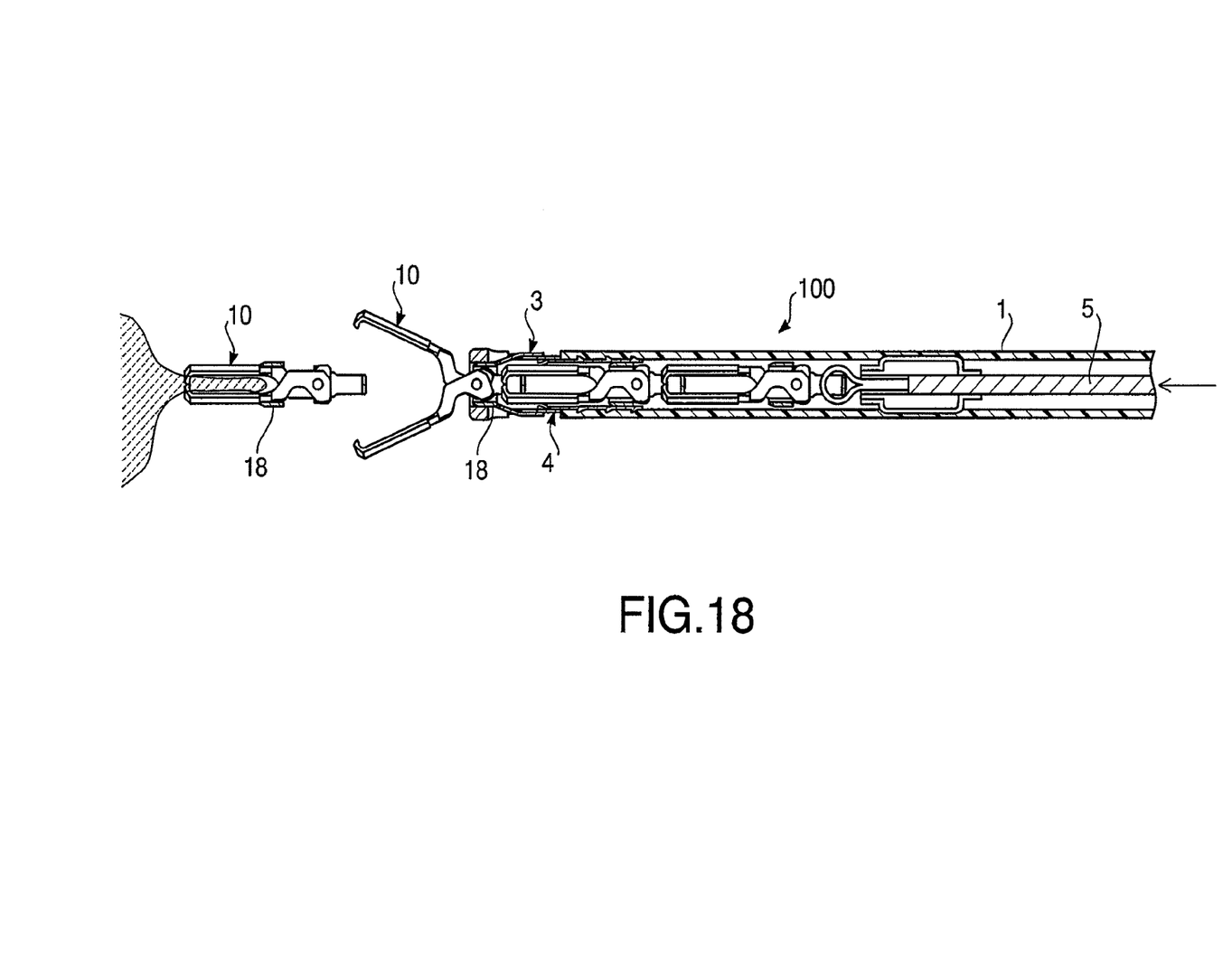
FIG. 18 shows a cross-sectional side view of the clipping instrument with the clip assembly being detached according to the embodiment of the present invention.

FIG. 18 shows a cross-sectional side view of the clipping instrument 100 with the clip assembly 10 being detached from a succeeding clip assembly 10 according to the embodiment of the present invention. When the operation wire 5 is again advanced forward, as shown in FIG. 18, the succeeding clip assembly 10, which is arranged in the next in line to follow the clip assembly 10 clutching onto the treatment area, is forwarded accordingly to project out of the sleeve 2, and the arms 11 are opened. Therefore, the front clip assembly 10 clutching onto the treatment area is released from the engagement with the arms 11 of the succeeding clip assembly 10. Thus, the front clip assembly 10 is detached from the clipping instrument 100 and remains in the patient body. The withdrawal stopper 3 returns to the original position according to the movement of the succeeding clip assembly 10.

The above-described procedure can be repeatedly applied to the second and the following clip assemblies 10 as may be necessary.

Although an example of carrying out the invention has been described above, the present invention is not limited to the above described embodiments. For example, a single clip assembly 10 may be provided instead of two or more clip assemblies 10 in the clipping instrument 100.

The present disclosure relates to the subject matter contained in Japanese Patent Application No. P2007-269731, filed on Oct. 17, 2007, which is expressly incorporated herein by reference in its entirety.

What is claimed is:

1. A clipping instrument for an endoscope, comprising:
a flexible sheath insertable into an instrument channel of the endoscope;
an operation wire, which is configured to be advanced and retracted in an axial direction of the flexible sheath;
at least one detachable clip assembly, including a pair of openable and closable clipping arms and a fastening ring that encircles proximal portions of the clipping arms, positioned in the vicinity of a distal end portion of the flexible sheath with the clipping arms closed, the clipping arms being configured to be projected forward to open outside the flexible sheath and to be closed to clip onto a treatment object outside the flexible sheath in accordance with advancing and retracting movements of the fastening ring with respect to the clipping arms, through the operation wire;
a withdrawal stopper, which is provided in the vicinity of the distal end portion of the flexible sheath; and
an advancement stopper, which is provided in the vicinity of the distal end portion of the flexible sheath, the advancement stopper being distinct from the withdrawal stopper;
wherein the withdrawal stopper restricts the fastening ring from being retracted rearward into the withdrawal stopper once the fastening ring is forwarded to extend through the withdrawal stopper; and
wherein the advancement stopper restricts the fastening ring from being advanced further to extend out of the advancement stopper once the fastening ring is advanced to extend through the withdrawal stopper.

2. The clipping instrument according to claim 1,
wherein the withdrawal stopper is axially movable with respect to the advancement stopper;
wherein the advancement stopper is at least partially fixed with respect to the flexible sheath; and
wherein the advancement stopper permits the fastening ring to advance further to extend out of the advancement stopper when the withdrawal stopper is moved rearward with respect to the advancement stopper according to the retracting movement of the fastening ring, which has once been advanced to extend through the withdrawal stopper.

3. The clipping instrument according to claim 2,
wherein the withdrawal stopper includes a pair of blade springs; and
wherein the advancement stopper includes an other pair of blade springs, which are radially expanded with respect to an axis of the flexible sheath.

4. The clipping instrument according to claim 3,
wherein the blade springs of the withdrawal stopper extend from a trunk portion of the withdrawal stopper toward a front of the clipping instrument, and front portions of the blade springs resiliently press sides of the clip assembly.

5. The clipping instrument according to claim 4,
wherein the pair of clipping arms are closed as the fastening ring, which is restricted from being advanced by the advancement stopper, is pushed forward by the operation wire due to transition of contact points of the fastening ring with the pair of clipping arms.

6. The clipping instrument according to claim 4,
wherein the pair of once opened clipping arms are closed as the fastening ring, which is restricted from being advanced by the advancement stopper, is retracted rearward by the operation wire due to transition of contact points of the fastening ring with the pair of clipping arms.

7. The clipping instrument according to claim 4,
wherein the advancement stopper is fixed with respect to the flexible sheath at a rear end portion thereof; and
wherein distal ends of the blade springs of the advancement stopper are angled inward so that the fastening ring is prevented from being further advanced when the withdrawal stopper is moved toward the front of the clipping instrument with respect to the advancement stopper to be in a tightening position.

8. The clipping instrument according to claim 7,
wherein the withdrawal stopper applies a tightening force to the advancement stopper to restrict the advancement of the fastening ring when the withdrawal stopper is moved to the tightening position to at least partially cover and resiliently tighten the blade springs of the advancement stopper; and wherein the advancement stopper is released from the tightening force when the withdrawal stopper is retracted rearward with respect to the advancement stopper in accordance with the retracting movement of the fastening ring and restored to be expanded so that the fastening ring is permitted to be advanced further to extend out of the advancement stopper.

9. The clipping instrument according to claim 3,
wherein the blade springs of the advancement stopper are provided in symmetric positions at approximately 180 degrees from each other;
wherein the blade springs of the withdrawal stopper are provided in symmetric positions at approximately 180 degrees from each other; and
wherein the withdrawal stopper and the advancement stopper are assembled together such that the blade springs of the withdrawal stopper are in positions approximately 90 degrees with respect to the blade springs of the advancement stopper, respectively.

10. The clipping instrument according to claim 2,
wherein the advancement stopper is restricted from being rotated about an axis of the flexible sheath.

11. The clipping instrument according to claim 2,
wherein the withdrawal stopper is restricted from being rotated about an axis of the flexible sheath.

12. The clipping instrument according to claim 11,
wherein the withdrawal stopper is restricted from being rotated with respect to the advancement stopper.

13. The clipping instrument according to claim 1, further comprising:
a sleeve, which is provided in the vicinity of the distal end portion of the flexible sheath and fixed to the flexible sheath, to support the advancement stopper and the withdrawal stopper.

14. The clipping instrument according to claim 13,
wherein the advancement stopper is fixed to the sleeve at least partially at a trunk portion of the advancement stopper; and
wherein the withdrawal stopper is axially movably fit around the advancement stopper.

15. The clipping instrument according to claim 13,
wherein the sleeve has a pair of slits, within which at least parts of the blade springs of the withdrawal stopper are movable, the pair of slits extending in the axial direction of the flexible sheath in symmetric positions at approximately 180 degrees from each other.

16. The clipping instrument according to claim 15,
wherein the sleeve has a pair of cutout portions, within which distal end portions of the advancement stopper are receivable, in symmetric positions at approximately 180 degrees from each other and at approximately 90 degrees from the respective slits.

17. The clipping instrument according to claim 16,
wherein the advancement stopper is assembled with the sleeve to have the distal end portions thereof aligned in a substantially same plane with a distal end portion of the sleeve.

18. The clipping instrument according to claim 1, wherein each of the advancement stopper and the withdrawal stopper comprises a generally polygonally shaped cylindrical member.

19. The clipping instrument according to claim 1, wherein the withdrawal stopper is movable axially with respect to the advancement stopper.

20. The clipping instrument according to claim 1, wherein an inner surface of a body portion of the withdrawal stopper is configured to receive an outer surface of the advancement stopper thereon.

* * * * *